(12) United States Patent
Chen et al.

(10) Patent No.: US 9,702,829 B1
(45) Date of Patent: Jul. 11, 2017

(54) SYSTEMS AND METHODS FOR WAFER SURFACE FEATURE DETECTION AND QUANTIFICATION

(71) Applicant: KLA-Tencor Corporation, Milpitas, CA (US)

(72) Inventors: Haiguang Chen, Mountain View, CA (US); Jaydeep Sinha, Livermore, CA (US); Sergey Kamensky, Campbell, CA (US); Enrique Chavez, Tracy, CA (US); Shouhong Tang, Santa Clara, CA (US); Mark Plemmons, Livermore, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/246,895

(22) Filed: Apr. 7, 2014

Related U.S. Application Data

(60) Provisional application No. 61/809,877, filed on Apr. 9, 2013, provisional application No. 61/835,437, filed on Jun. 14, 2013.

(51) Int. Cl.
*G01B 9/02* (2006.01)
*G01N 21/95* (2006.01)
*G01N 21/956* (2006.01)
*G01B 11/30* (2006.01)

(52) U.S. Cl.
CPC ....... *G01N 21/9501* (2013.01); *G01N 21/956* (2013.01); *G01B 11/30* (2013.01); *G01B 11/303* (2013.01); *G01B 11/306* (2013.01)

(58) Field of Classification Search
CPC ..... G01B 11/30; G01B 11/303; G01B 11/306; G01N 21/9501; G01N 21/956

USPC .................................. 356/450, 237.2–237.5
See application file for complete search history.

(56) References Cited

U.S. PATENT DOCUMENTS

| 6,847,458 | B2 | 1/2005 | Freischlad et al. |
| 7,664,310 | B2 | 2/2010 | Emery et al. |
| 7,667,852 | B2 | 2/2010 | Tang |
| 7,796,273 | B2 | 9/2010 | Deck et al. |

(Continued)

OTHER PUBLICATIONS

Dr. Munther Gdeisat and Dr Francis Lilley, One-Dimensional Phase Unwrapping Problem, Printed online at: http://www.ljmu.ac.uk/GERI/CEORG_Docs/OneDimensionalPhaseUnwrapping_Final.pdf, 11 pages, Print Date Apr. 7, 2014.

(Continued)

*Primary Examiner* — Hina F Ayub
(74) *Attorney, Agent, or Firm* — Suiter Swantz pc llo

(57) ABSTRACT

Interferometer systems and methods for providing improved defect detection and quantification are disclosed. The systems and methods in accordance with the present disclosure may detect surface defects on patterned or bare wafer surfaces and subsequently quantify them. In certain embodiments in accordance with the present disclosure, amplitude maps of the wafer surfaces are obtained and are utilized in addition/alternative to phase maps for wafer surface feature detection. Furthermore, local one-dimensional and/or two-dimensional unwrapping techniques are also disclosed and are utilized in certain embodiments in accordance with the present disclosure to provide height and depth information of the detected defects, further improving the detection capabilities of the measurement systems.

25 Claims, 13 Drawing Sheets

(56) References Cited

U.S. PATENT DOCUMENTS

| | | | |
|---|---|---|---|
| 7,796,275 B2 | 9/2010 | Deck et al. | |
| 2003/0035113 A1* | 2/2003 | Wang et al. | 356/491 |
| 2003/0155537 A1* | 8/2003 | Machavariani | G01N 21/21 |
| | | | 250/559.27 |
| 2004/0257587 A1* | 12/2004 | Rosakis | G01B 9/02 |
| | | | 356/520 |
| 2007/0146685 A1* | 6/2007 | Yoo et al. | 356/32 |
| 2009/0284734 A1* | 11/2009 | Tang | G01B 11/0608 |
| | | | 356/73 |
| 2012/0177282 A1 | 7/2012 | Chen et al. | |
| 2014/0063024 A1* | 3/2014 | Zhang et al. | 345/506 |

OTHER PUBLICATIONS

Dr. Munther Gdeisat and Dr Francis Lilley, Two-Dimensional Phase Unwrapping Problem, Printed online at: https://www.ljmu.ac.uk/GERI/CEORG_Docs/Two_Dimensional_Phase_Unwrapping_Final.pdf, 32 pages, Print Date Apr. 7, 2014.

* cited by examiner

SYSTEMS AND METHODS FOR WAFER SURFACE FEATURE DETECTION AND QUANTIFICATION

CROSS-REFERENCE TO RELATED APPLICATIONS

The present application claims the benefit under 35 U.S.C. §119(e) of U.S. Provisional Application Ser. No. 61/809,877, filed Apr. 9, 2013. Said U.S. Provisional Application Ser. No. 61/809,877 is hereby incorporated by reference in its entirety.

The present application also claims the benefit under 35 U.S.C. §119(e) of U.S. Provisional Application Ser. No. 61/835,437, filed Jun. 14, 2013. Said U.S. Provisional Application Ser. No. 61/835,437 is hereby incorporated by reference in its entirety.

TECHNICAL FIELD

The disclosure generally relates to the field of wafers, and particularly to systems and methods for wafer surface feature/defect detection and quantification.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks and the like. While the technique described here refers mainly to wafers, it is to be understood that the technique also is applicable to other types of polished plates as well. The term wafer and the term thin polished plate may be used interchangeably in the present disclosure.

Generally, certain requirements may be established for the flatness and thickness uniformity of the wafers. There exist a variety of techniques to address the measurement of shape and thickness variation of wafers. However, most existing wafer inspection tools can only inspect the wafer surface and detect the surface defects. Some wafer surface inspection tools may also calculate the defect areas and classify the defect types, but there is no information reported about the defect height or depth by the existing inspection tools.

SUMMARY

The present disclosure is directed to a method for inspecting a wafer. The method includes: acquiring a set of intensity frames of at least one portion of a surface of the wafer; extracting an amplitude map of said at least one portion of the surface of the wafer based on said set of intensity frames; and performing defect detection based on the amplitude map.

A further embodiment of the present disclosure is also directed to a method for inspecting a wafer. The method includes: acquiring a set of intensity frames of a surface of the wafer; extracting a phase map of at least one region of interest of the surface of the wafer based on said set of intensity frames; unwrapping the phase map utilizing a local one-dimensional phase unwrapping process, wherein the local one-dimensional phase unwrapping process is performed based on a plurality of linear unwrapping paths defined within said at least one region of interest; and performing defect detection based on the unwrapped phase map.

An additional embodiment of the present disclosure is directed to a method for inspecting a wafer. The method includes: acquiring a set of intensity frames of a surface of the wafer; extracting a phase map of at least one region of interest of the surface of the wafer based on said set of intensity frames; unwrapping the phase map utilizing a local two-dimensional phase unwrapping process, wherein the local two-dimensional phase unwrapping process is performed for said at least one region of interest; and performing defect detection based on the unwrapped phase map.

An additional embodiment of the present disclosure is directed to an interferometer system. The interferometer system includes: an interferometer configured for acquiring a set of intensity frames of a surface of a wafer, and a wafer surface feature detection module in communication with the interferometer. The wafer surface feature detection module is configured to: extract at least one of: an amplitude map of the surface of the wafer based on said set of intensity frames; and a phase map of at least one region of interest of the surface of the wafer based on said set of intensity frames; and perform defect detection based on said at least one of: the amplitude map and the phase map.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Figure 1:
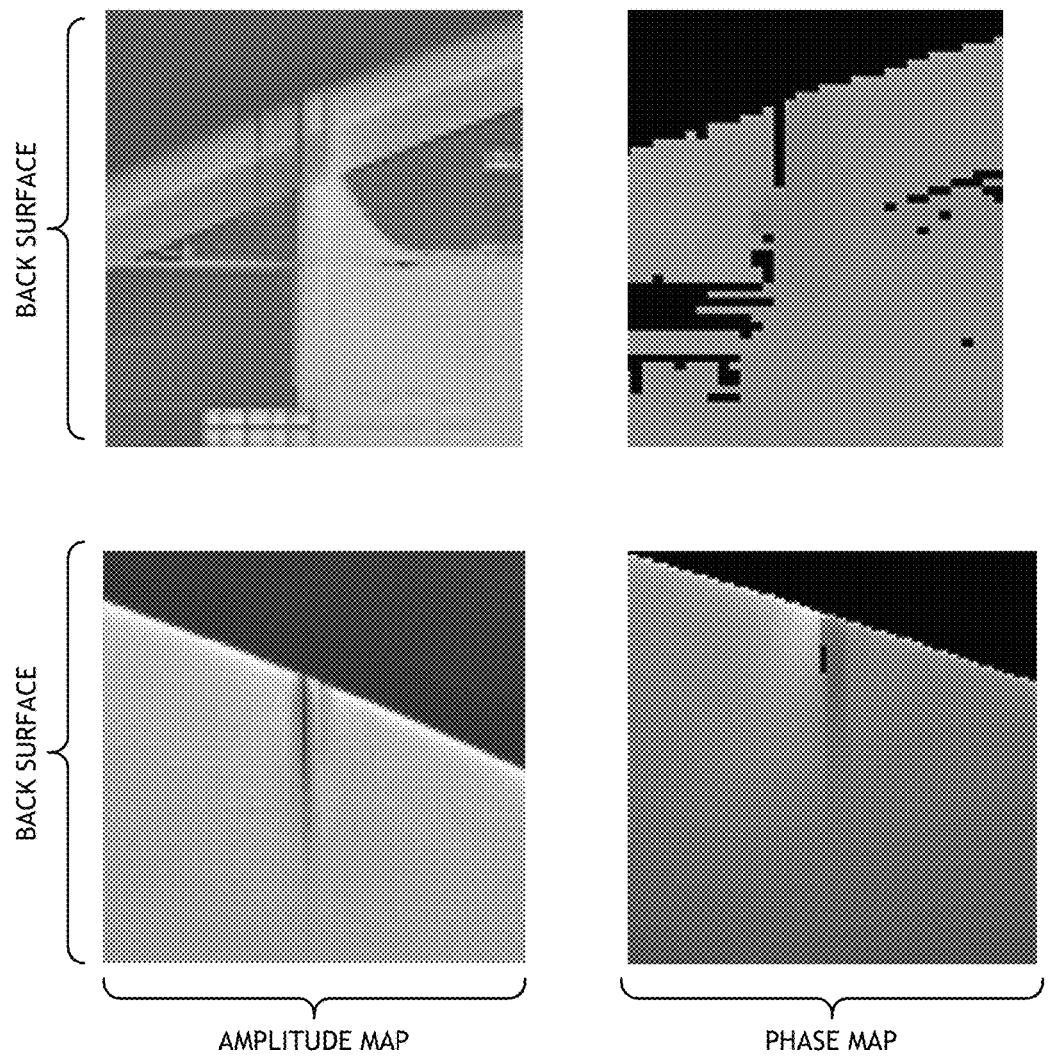
FIG. 1 is an illustration depicting amplitude maps and phase maps of a front surface and a back surface of a portion of a wafer.

Reference will now be made in detail to the subject matter disclosed, which is illustrated in the accompanying drawings.

Silicon wafers are available in a variety of sizes. They may also be patterned or presented as bare wafers. Wafer metrology tools and interferometer systems, such as WaferSight metrology system from KLA-Tencor (disclosed in U.S. Pat. No. 6,847,458, the disclosure of which is incorporated herein by reference in its entirety), may scan both the front and back surfaces of a wafer at the same time. By combining wafer shape, edge roll-off, thickness or flatness, and topography measurements in a single scan, such wafer metrology tools may provide complete data sets that are necessary for wafer topography and geometry monitoring in wafer manufacturing.

The present disclosure is directed to systems and methods for providing improved defect detection and quantification capabilities for systems such as wafer metrology tools and interferometer systems. The systems and methods in accordance with the present disclosure may detect surface defects on patterned or bare wafer surfaces and subsequently quantify them. In certain embodiments in accordance with the present disclosure, amplitude maps of the wafer surfaces are obtained and are utilized in addition, or alternatively, to phase maps for wafer surface feature detection. Furthermore, local one-dimensional and/or two-dimensional unwrapping techniques are also disclosed and are utilized in certain embodiments in accordance with the present disclosure to provide height and depth information of the detected defects, further improving the detection capabilities of the measurement systems.

This portion of the description will first describe utilizing an amplitude map of a wafer surface generated based on data obtained from an interferometer for defect detection. It is noted that the intensity recorded directly from an interferometer at position (x,y) can be expressed as:

$$I(x,y) = a(x,y) + b(x,y) \cos[\phi(x,y)]$$

Where:

a(x,y) is the background intensity that is related to the reflectance amplitude of both reference and object surfaces;

b(x,y) is the amplitude of the interferometric fringes, which is also related to the reflectance amplitude of both reference and object surfaces, and more importantly, it is related to the slope of measuring surface; and $\phi(x,y)$ is the phase of the interferometric fringes that is related to the optical path difference of the reference and the object (e.g., the measuring wafer) as well as the reflection phase difference between reference and object surfaces. Because the phase of a wave reflected from a surface depends on the surface optical property n&k, the interferometric fringe phase therefore cannot properly represent the measuring absolute surface height if the n&k changes over the field of view. However, the measured relative surface height variation does provide very useful information for the die-to-die or wafer-to-wafer surface variation monitoring.

The relationship between the fringe amplitude and the measuring surface slope can be written as:

$$b(x, y) = R(x, y) \text{sinc}\left(\frac{2L_x \frac{\partial z(x, y)}{\partial x}}{\lambda}\right) \text{sinc}\left(\frac{2L_y \frac{\partial z(x, y)}{\partial y}}{\lambda}\right) MTF\left(\frac{\partial z(x, y)}{\partial x}, \frac{\partial z(x, y)}{\partial y}\right)$$

Where:

R(x,y) is related to the surface optical property n&k;

MTF( ) is related to the optical system MTF that is a function of surface slopes; and $L_x$ and $L_y$ are the surface samplings in x direction and y direction, respectively.

It is noted that the fringe amplitude map can be generated robustly using phase shift technologies, and it does not require phase unwrapping necessary for generating phase maps. Using amplitude maps therefore helps avoiding errors associated with conventional phase unwrapping processes. It is also noted that in the above equation, both sinc function and MTF function values decrease as the surface slope increases. This implies that the fringe amplitude at a position, where the surface slope has sudden changes or is much larger than the surrounding area, is much smaller than its neighboring area in the amplitude map so that it can be detected. The fringe phase at this position, however, may not be able to catch such sudden slope changes. This is because the fringe phase computation in phase shift technology, by design, may be insensitive to the fringe amplitude change so that it may be insensitive to such sudden slope change.

For example, a type of wafer defect called a slip is depicted in both the amplitude map and the phase map in FIG. 1. Since the slip has sudden slope changes, it is clearly shown in both the front and the back side of amplitude maps. Although the back surface phase map also has some information related to the slip, the large slope causes the pixel drop out to lose sensitivity and robustness for effective detection of the slip. In the front surface phase map (e.g., the patterned side of phase map), on the other hand, the slip information disappears due to conventional phase unwrapping errors. Therefore, in such situations, the amplitude maps provide very useful information for feature/defect detection.

Figure 2:
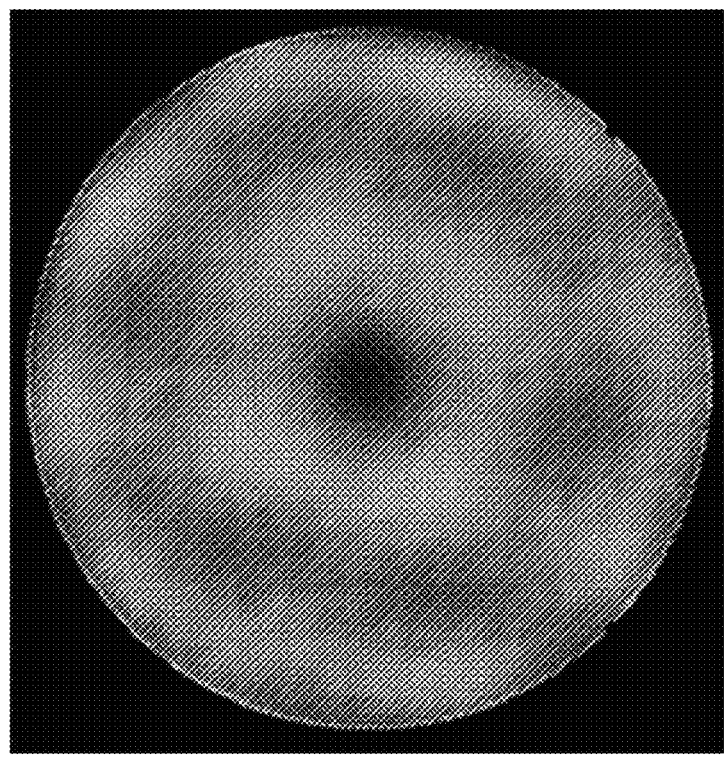
FIG. 2 is an illustration depicting an amplitude map and a phase map of a surface of a wafer.
Figure 2:

It is understood that amplitude maps are useful for other types of feature/defect detections as well. Amplitude maps are sensitive to any defects where the surface has sudden slope changes and sudden refraction index (n&k) variations. In another example as depicted in FIG. 2, the amplitude map and the phase map generated from the same set of phase-shifted interferograms are shown. In this example, the amplitude map provides rich wafer information that the phase map does not have. Thus, the amplitude map can be utilized for detecting defects such as sudden film, slope, material changes and the like on wafer surfaces without departing from the spirit and scope of the present disclosure.

Figure 3:
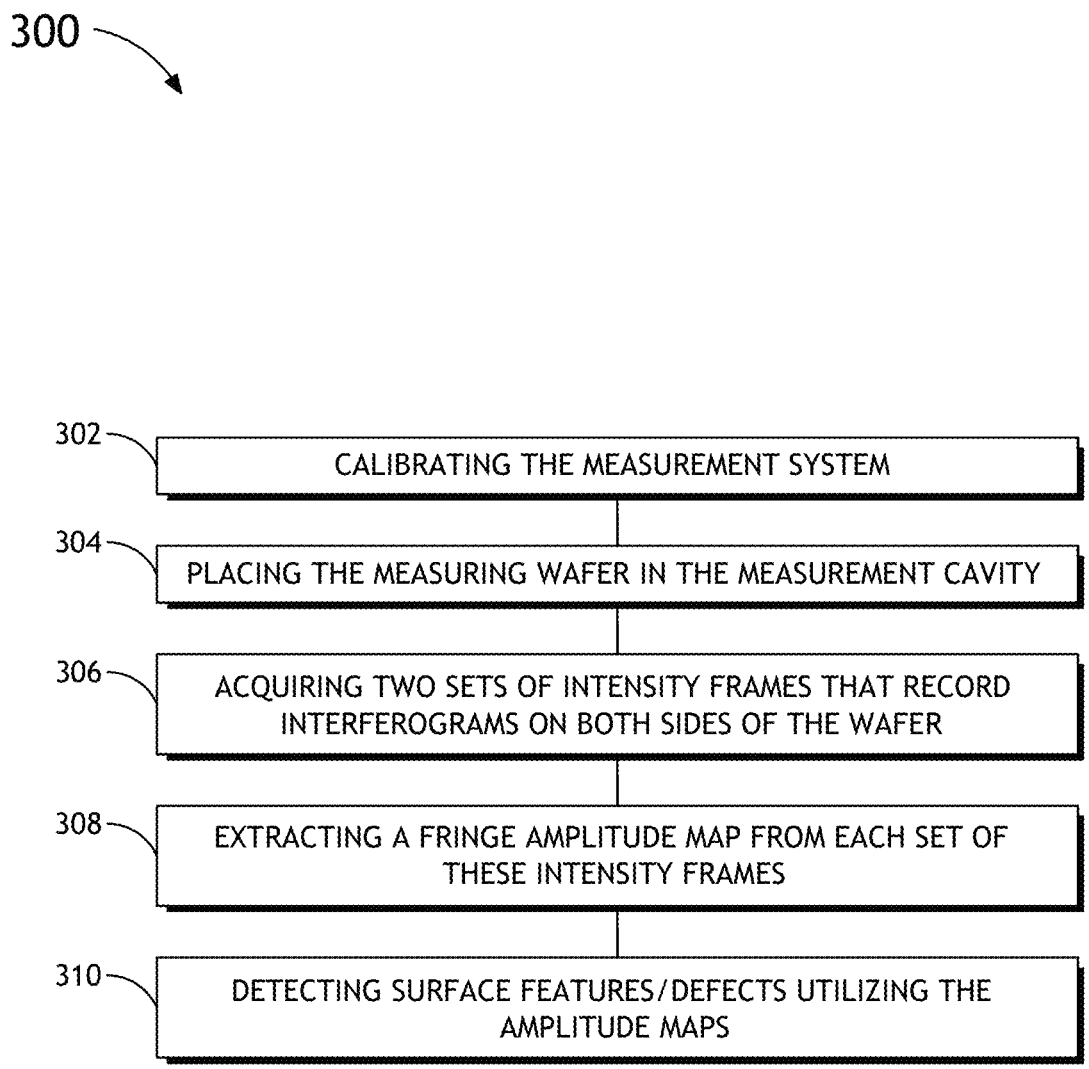
FIG. 3 is a flow diagram illustrating a method for wafer feature/defect detection utilizing an amplitude map.

FIG. 3 is a flow diagram illustrating a method 300 for wafer feature/defect detection utilizing, at least partially, the amplitude maps. In one embodiment, the measurement system may be calibrated in step 302. The calibration process may calibrate the phase shifting speed and the measurement cavity characteristics of the measurement system. The wafer to be measured, referred to as the measuring wafer, may then be placed in the cavity in step 304. Two sets of intensity frames that record interferograms on both sides of the wafer may be acquired in step 306, and a fringe amplitude map may then be extracted from each set of these intensity frames in step 308. Subsequently, the amplitude maps can be used for feature/defect detection in step 310 as previously described.

It is contemplated that the feature/defect detection process as described above is not limited to utilizing only the amplitude maps. That is, phase maps may also be extracted along with the amplitude maps from each set of these intensity frames in step 308, and the amplitude maps and the phase maps can be used jointly for feature/defect detection in step 310. It is also contemplated that various detection algorithms, such as local peak and valley, local root mean square, local slope or curvature, filtering, as well many other local surface metrics from other techniques may be utilized without departing from the spirit and scope of the present disclosure.

It is further contemplated that the feature/defect detection method as described above is not required to perform feature/defect detection on both surfaces of the wafer. That is, method 300 may be configured to perform feature/defect detection on either or both sides of the wafer without departing from the spirit and scope of the present disclosure.

Figure 4:
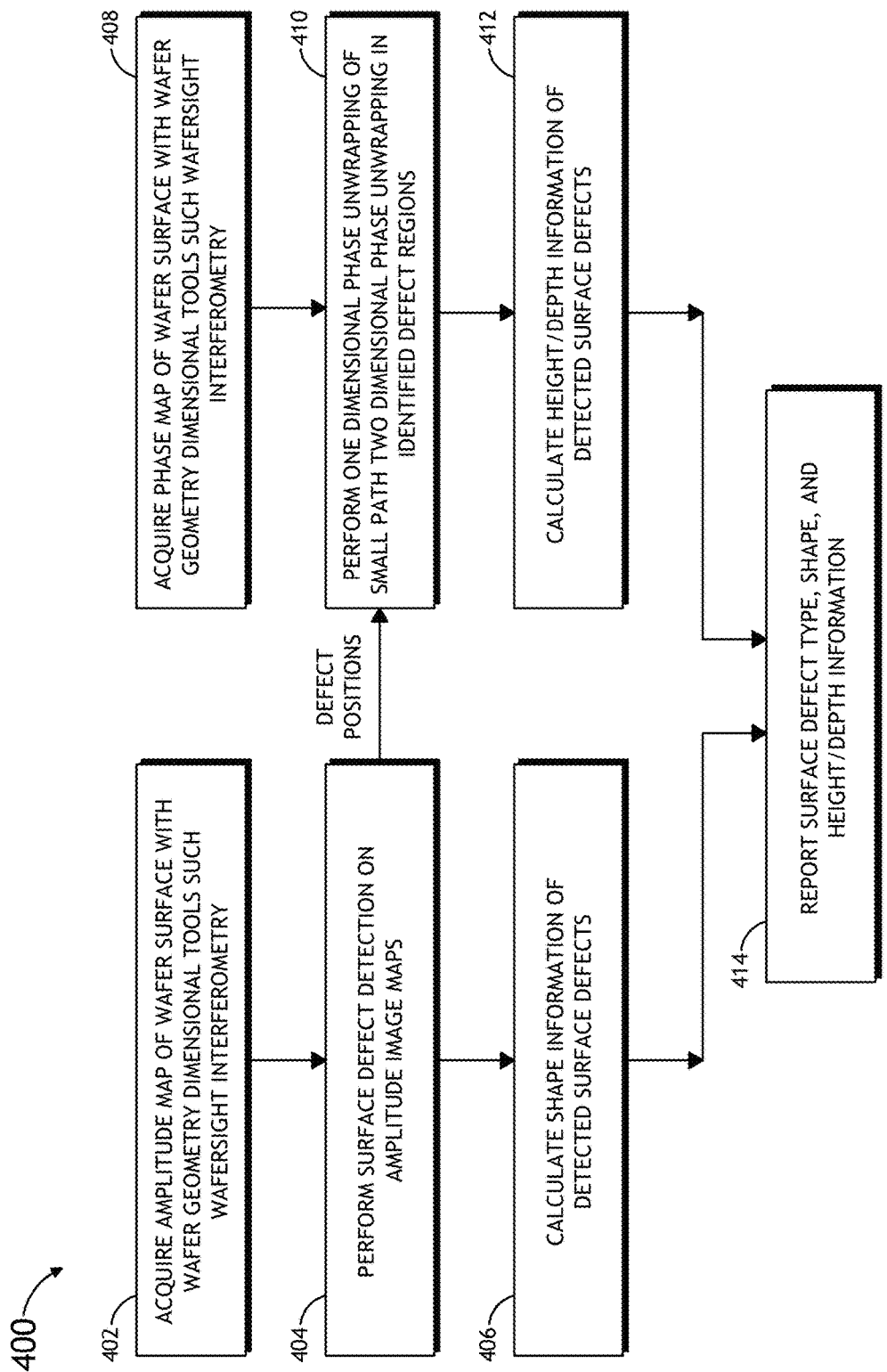
FIG. 4 is a flow diagram illustrating a method for wafer feature/defect detection utilizing both intensity and amplitude maps of a wafer surface.

It is noted that while the amplitude maps are sensitive to defects and sudden slope changes, and are therefore very useful for defect detection, height/depth information of the detected defects cannot be obtained from such amplitude maps. To obtain height/depth information of the detected defects, phase maps are still needed. Referring generally to FIG. 4, a flow diagram illustrating a method 400 utilizing both amplitude and phase maps of a wafer surface for wafer surface geometry analysis is shown. Steps 402 through 406 have been described above, wherein amplitude maps are generated based on acquired interferograms and used for feature/defect detection. It is noted that the regions identified as being defective in step 404 (which may be referred to as defective regions or regions of interest) may be reported and further processed utilizing their corresponding phase maps in order to obtain their height/depth information, as depicted in steps 408 and 410 of FIG. 4.

More specifically, the phase maps can be constructed from acquired video frames with different phase shifts in the measurement system. As depicted in FIG. 4, the shape information, such as area, length, and orientation of the detected defects can be calculated and reported for defect classification. The defect positions are sent to a phase unwrapping module to reconstruct the local surface height profiles in the defect regions in step 410, from which, the height/depth information of the detected surface defects can be calculated in step 412 and then reported for the defect classification and quantification in step 414.

As mentioned previously, however, conventional phase unwrapping processes can introduce errors and adversely affect the detection and quantification accuracies. For instance, due to the sharp surface geometry changes in the defect region, conventional phase unwrapping processes often fail to accurately reconstruct the wafer surface height map from the wrapped phase map in the defect regions of several important defects, resulting in many invalid data regions and inaccurate defect shapes, and thus severely affecting the accurate defect detection and quantification. Conventional two-dimensional phase unwrapping processes used for wafer surface reconstruction may also fail to generate satisfying wafer surface height maps on the pattern side, due to the sharp surface topography changes. It is noted, therefore, that the phase unwrapping module utilized in step 410 differs from conventional phase unwrapping processes in several respects and provides several improvements.

This portion of the description will describe several exemplary embodiments of the phase unwrapping module utilized in step 410. More specifically, a local one-dimensional phase unwrapping module, a local two-dimensional phase unwrapping module, as well as an integration technique will be described in details below.

It is noted that local phase unwrapping techniques can be beneficial because, for many applications of the wafer surface geometry, the exact wafer surface height information is not required, only the local defect height/depth relative to the neighborhood background is needed. Performing phase unwrapping locally will effectively detect and quantify the wafer surface defects, and avoid the serious problems in the whole wafer phase unwrapping, which is only required for obtaining the exact wafer shape information.

Figure 5:
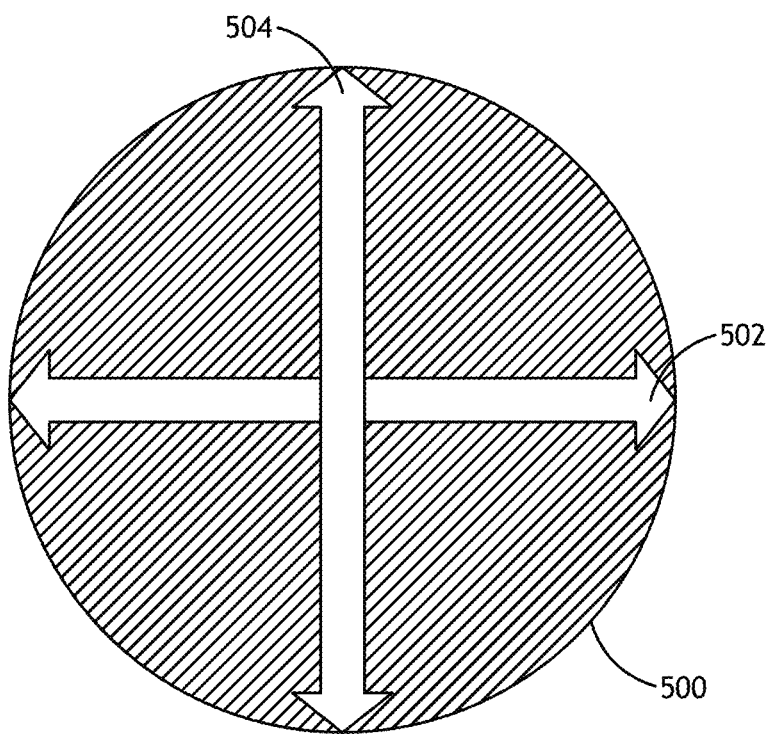
FIG. 5 is an illustration depicting phase unwrapping paths for a local one-dimensional phase unwrapping process for a disk shaped defect.
Figure 6:
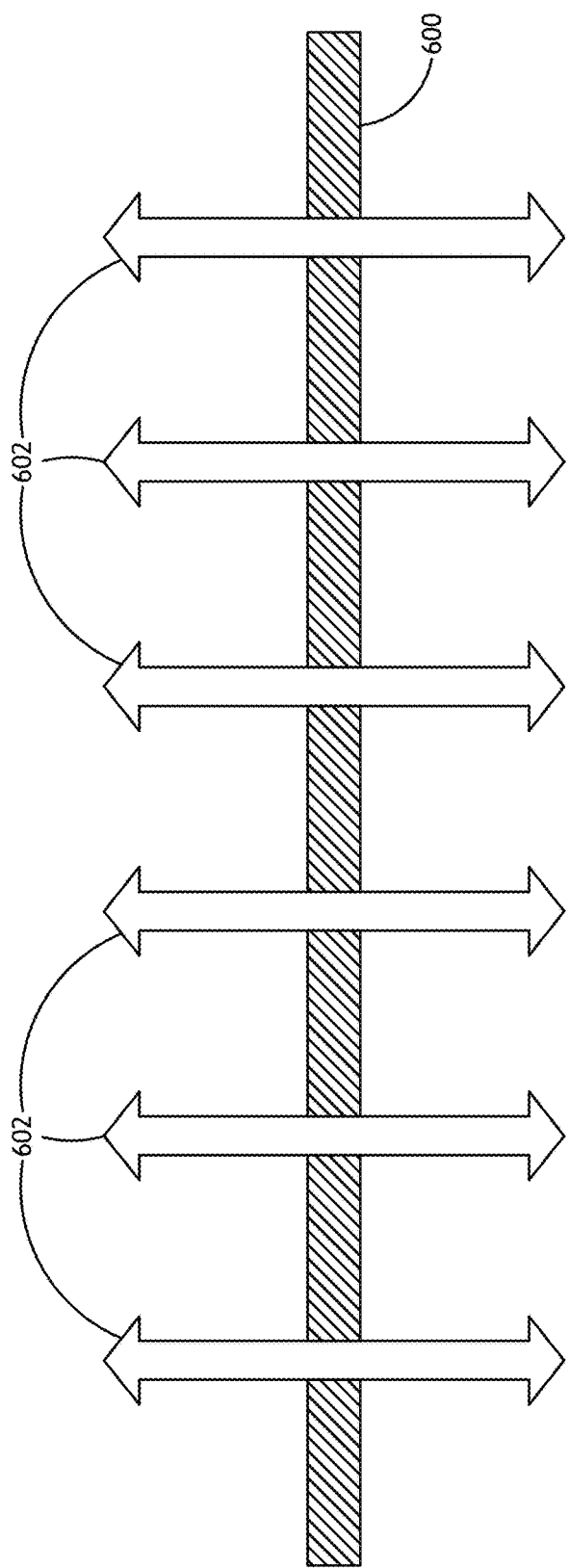
FIG. 6 is an illustration depicting phase unwrapping paths for a local one-dimensional phase unwrapping process for an extended line defect.

In one embodiment, a process referred to as local one-dimensional (1D) phase unwrapping is utilized in step 410. Referring generally to FIGS. 5 and 6, different paths for one-dimensional phase unwrapping can be selected according to the particular detected defect regions from intensity/amplitude maps. For example, if the defect region is a disk shape defect 500 as shown in FIG. 5, the unwrapping paths can start from the defect centroid and end at the defect boundaries in several major directions 502 and 504. In another example as shown in FIG. 6, for a line shaped defect 600, the one-dimensional phase unwrapping paths 602 can start from one side of the line and end on other side in the orthogonal directions of the line orientation. It is contemplated that other defect shapes can select different one-dimensional phase unwrapping paths for different coverage. In this manner, the defect height/depth information can be extracted from the acquired phase map and reported as maximum height/depth, mean height/depth, or median height/depth for the defect quantification.

It is noted that this process is referred to as local one-dimensional phase unwrapping in the present disclosure because it is performed locally within proximity to each detected defect region, as opposed to a wafer as a whole. In addition, the phase unwrapping process itself is a one-dimensional process because each phase unwrapping is performed according to a one-dimensional path (as depicted in the examples shown in FIGS. 5 and 6). It is contemplated that various one-dimensional phase unwrapping techniques may be utilized to perform each specific unwrapping process, without departing from the spirit and scope of the present disclosure.

Figure 7:
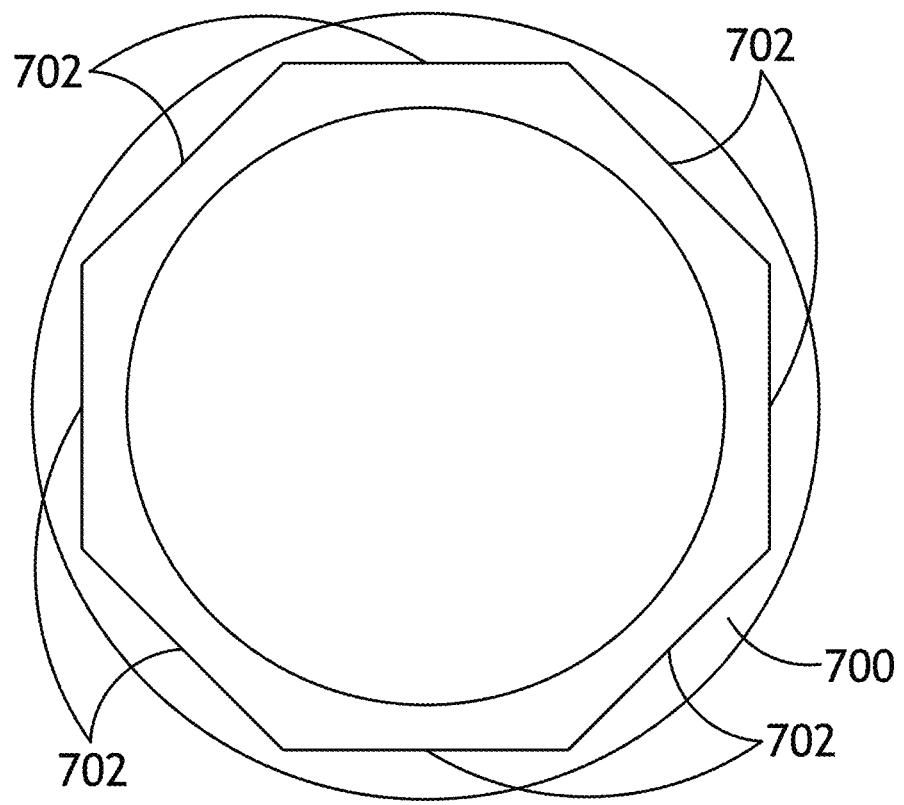
FIG. 7 is an illustration depicting phase unwrapping paths for a local one-dimensional phase unwrapping process along the wafer edge.

FIG. 7 depicts another example of one-dimensional phase unwrapping. This one-dimensional phase unwrapping scheme is suitable for wafer edge region 700 defect detection and quantification. Generally, in the wafer edge roll off regions, surface slope in the radial direction is much higher than in the tangential direction, thus the phase gradient is also much higher in the radial direction. With addition of the surface defects, which increase the local surface slope, there are often phase unwrapping errors in the wafer edge defect regions, resulting in missing data and severe shape distortions. By performing the one-dimensional phase unwrapping in the tangential direction along the paths 702 (or several major orientations parallel to the paths 702) as shown in FIG. 7, the wafer edge region is converted into polar space in different surface sectors, allowing one-dimensional phase unwrapping to be performed locally for each sector.

Figure 8:
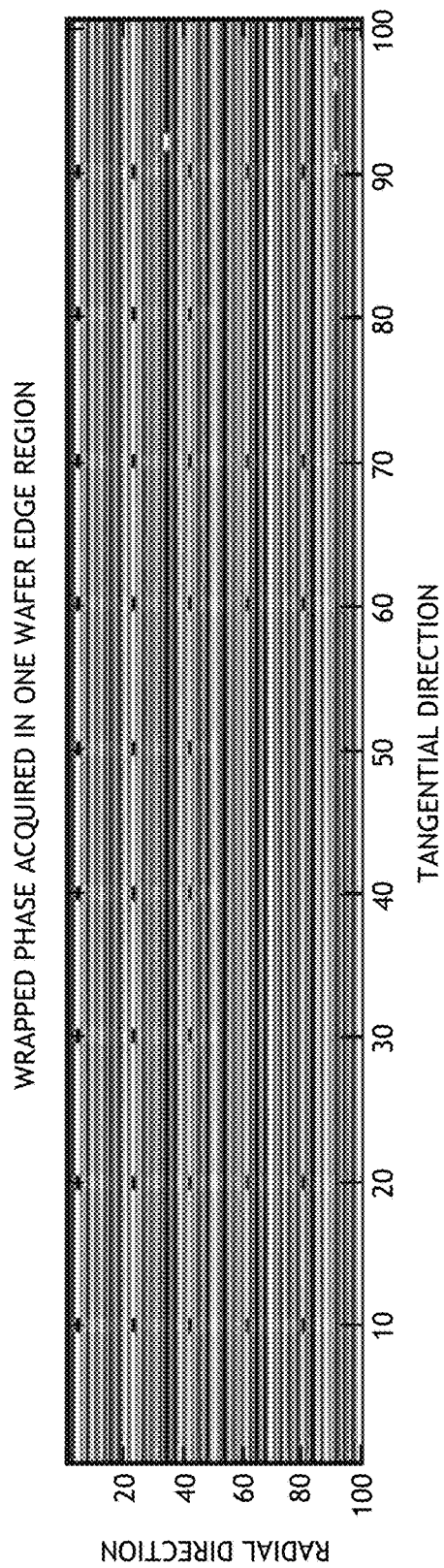
FIG. 8 is an illustration depicting a wrapped phase acquired in a wafer edge region.
Figure 9:
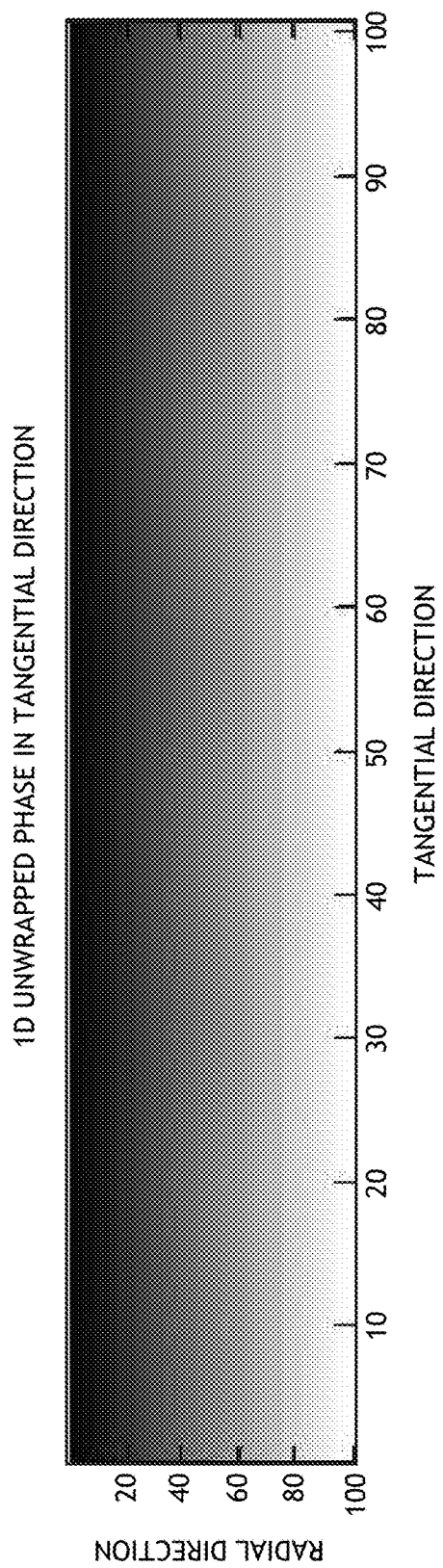
FIG. 9 is an illustration depicting a one-dimensionally unwrapped phase of the wafer edge region of FIG. 8.
Figure 10:
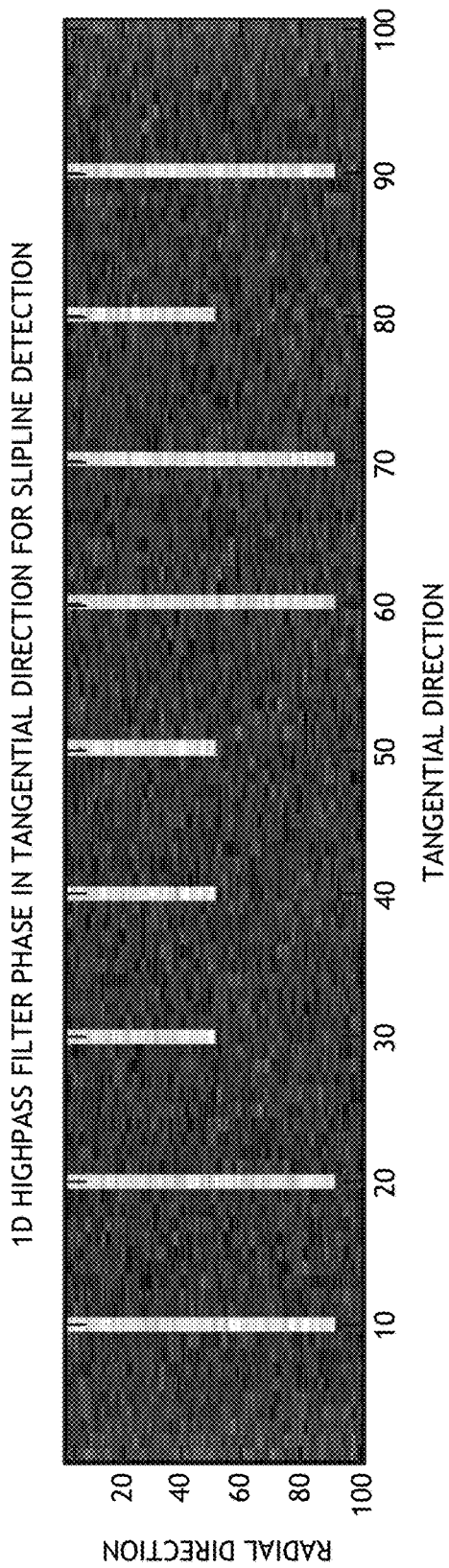
FIG. 10 is an illustration depicting the unwrapped phase filtered using a high-pass filter.

In FIG. 7, eight major directions are selected to perform the one-dimensional phase unwrapping, and more directions can be used if higher angular characteristic adaption is required. Since the phase map has much lower gradient in the tangential direction, much improved surface reconstruction and defect shape definition in the wafer edge region can be obtained as shown in FIGS. 8-10. More specifically, FIG. 8 shows a wrapped phase acquired in one wafer edge region, FIG. 9 shows the phase information shown in 8 unwrapped according to a unwrap path, and FIG. 10 shows the unwrapped phase filtered using a high-pass filter. For the slipline detection at the wafer edge region, the acquired phase data segment $P(r1:r2,\theta1:\theta2)$ in the polar space, as shown in FIG. 8, can be unwrapped using one-dimensional (1D) phase unwrapping first in $\theta$ direction:

$$\overline{P}(r,\theta1:\theta2)=\text{Unwrap}_{1D}[P(r,\theta1:\theta2)], \text{ for } r=r1:r2.$$

The unwrap function, $\text{Unwrap}_{1D}$, here corrects the radian phase angles in the given phase vector $P(r,\theta1:\theta2)$ by adding multiples of $\pm 2\pi$ when the absolute jumps between consecutive elements of $P(r,\theta1:\theta2)$ are greater than or equal to the jump tolerance of $\pi$ radian. The result is shown in the FIG. 9. Then one dimensional high-pass filtering with the filter length L in $\theta$ direction can be carried out on the unwrapped phase row by row to obtain the contrast enhanced signal for effective slipline detection:

$$FP(r,\theta1:\theta2)=\overline{P}(r,\theta1:\theta2)-\text{MedianFilter}(\overline{P}(r,\theta1:\theta2),L),$$
$$\text{for } r=r1:r2$$

as shown in FIG. 10. Subsequently, the unwrapped, filtered phase can then be used directly for the surface defect detection and quantification, even if the intensity/amplitude maps are not available.

Alternative to the local one-dimensional phase unwrapping process as describe above, in one embodiment, a process referred to as local two-dimensional (2D) phase unwrapping is utilized in step 410. Depending on the applications, different local processing area (which may be referred to as a small patch) of the image region can be used to perform the local phase unwrapping and the corresponding different filtering schemes can be used to extract the required surface information.

Figure 11:
FIG. 11 illustrates an example of local geometry analysis utilizing a 3×3 image patch.
Figure 12:
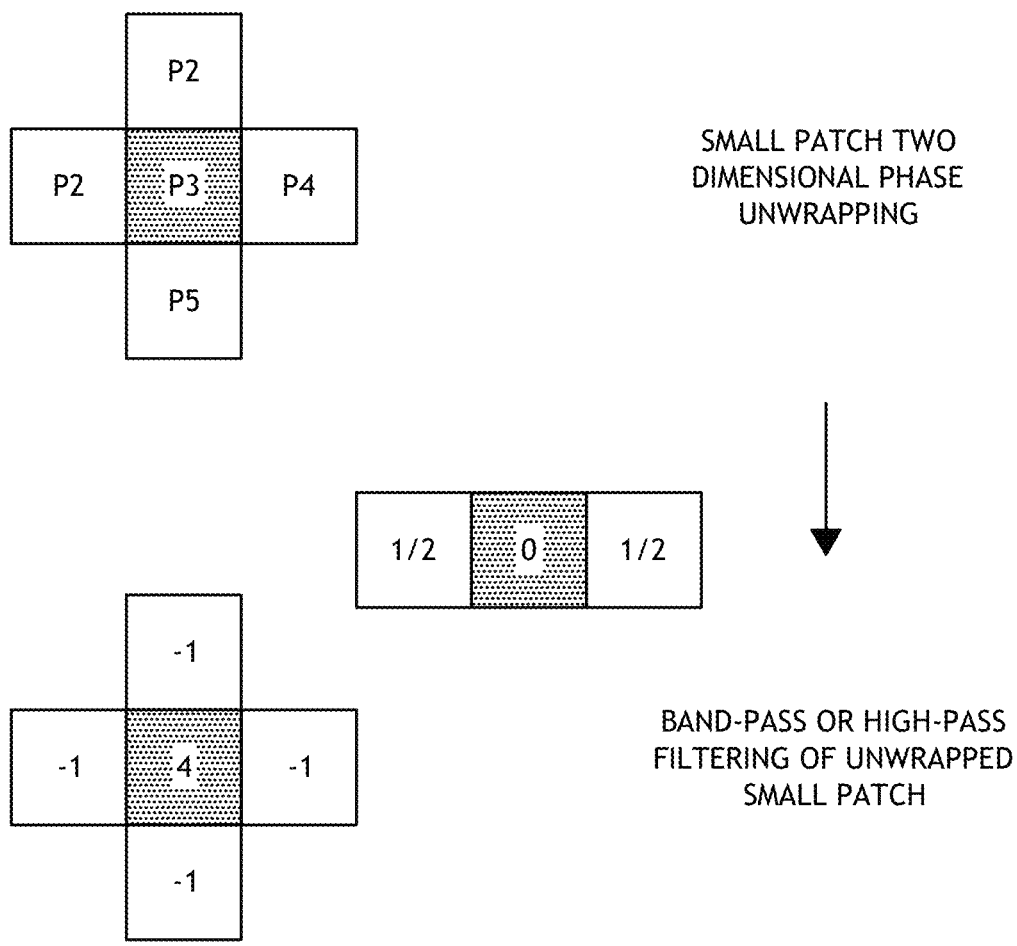
FIG. 12 illustrates an example of local geometry analysis utilizing a cross-shaped image patch.

Referring to FIG. 11, an example of local geometry analysis utilizing a 3×3 image patch is used to perform the local two-dimensional phase unwrapping from the center pixel P5. Subsequently, a 3×3 Laplace filter is applied to the unwrapped image patch. Another example, as depicted in FIG. 12, shows a cross-shaped image patch used to unwrap the phase from the center pixel P3 and the corresponding 5-pixel high-pass filter is applied on the unwrapped image patch. For overlay error analysis, the cross-shaped image patch can be used to unwrapped the phase, and two one-dimensional three-pixel filters can then be used to calculate the local surface slopes in x- and y-directions, respectively.

More specifically, for a given pixel position (x,y), the phase values of five pixels in the cross-shaped local patch can be expressed as:

$$P(x,y+1)$$

$$P(x-1,y) P(x,y) P(x+1,y)$$

$$P(x,y-1)$$

The corresponding local unwrapped cross patch is formed as:

$$\overline{P}(x,y+1)$$

$$\overline{P}(x-1,y) \overline{P}(x,y) \overline{P}(x+1,y)$$

$$\overline{P}(x,y-1)$$

Where the five unwrapped phase values in this small patch are calculated as:

$$\overline{P}(x,y)=P(x,y)$$

$$\overline{P}(x-1,y)=P(x,y)+\text{Unwrap}_{1D}[P(x-1,y)-P(x,y)]$$

$$\overline{P}(x+1,y)=P(x,y)+\text{Unwrap}_{1D}[P(x+1,y)-P(x,y)]$$

$$\overline{P}(x,y-1)=P(x,y)+\text{Unwrap}_{1D}[P(x,y-1)-P(x,y)]$$

$$\overline{P}(x,y+1)=P(x,y)+\text{Unwrap}_{1D}[P(x,y+1)-P(x,y)]$$

Here, the unwrap function $\text{Unwrap}_{1D}$ corrects the phase angle difference by adding multiples of $\pm 2\pi$ when the absolute phase jumps between these two phase values are greater than or equal to the jump tolerance of $\pi$ radian. Then the phase slopes in the X and Y directions can be calculated using these unwrapped phase values as follows:

$$\text{Slope}_x(x,y) = \frac{\overline{P}(x+1,y)-\overline{P}(x-1,y)}{2\Delta_x},$$

$$\text{Slope}_y(x,y) = \frac{\overline{P}(x,y+1)-\overline{P}(x,y-1)}{2\Delta_y}.$$

where $\Delta_x$ and $\Delta_y$ are pixel sizes in x and y directions, respectively.

Figure 13:
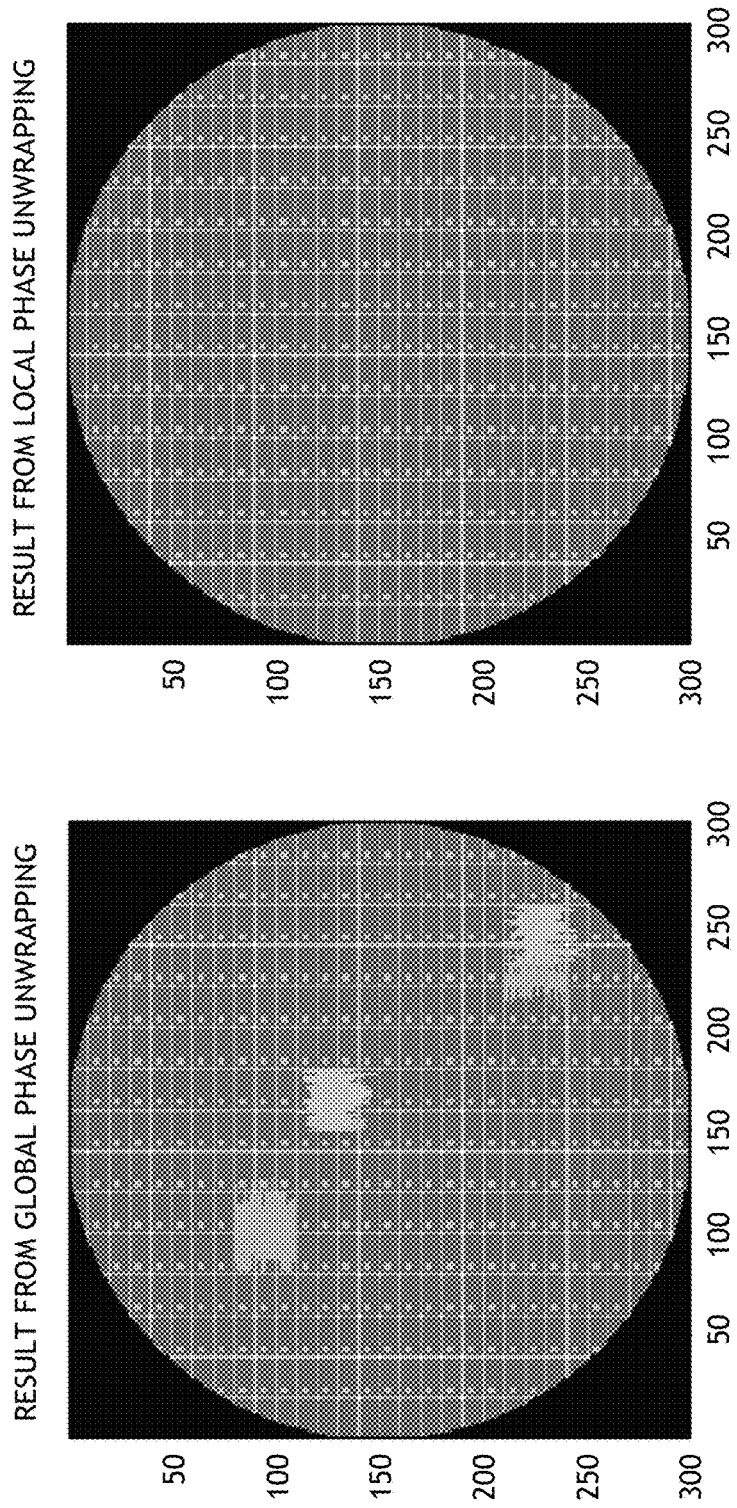
FIG. 13 illustrates a reduction of errors associated with local phase unwrapping compared to errors associated with conventional global phase unwrapping.

In one embodiment, this small patch two-dimensional phase unwrapping process is performed for each pixel within a detected defect region to unwrap the two-dimensional phase information for that region. While both these two phase unwrapping operations discussed above are performed only in one direction only for each phase pixel value, for general small patch phase unwrapping, two-dimensional phase unwrapping needs to be carried out to remove the phase jumps in the given local phase patch. It is also contemplated that this small patch two-dimensional phase unwrapping process may be performed for each pixel of the entire wafer image so as to produce an integrated, unwrapped and filtered phase map of the entire wafer. Such a process can be very useful for obtaining the geometry images for both bare and patterned wafers, with significant error reduction compared to conventional global phase unwrapping as shown in FIG. 13. This is due to the important fact that any phase unwrapping error in the general two-dimensional phase unwrapping will be accumulated and propagated in the phase unwrapping process, while any phase unwrapping error in the local phase unwrapping will be local and therefore bounded both in location and magnitude. As depicted in FIG. 13, it is clear that global phase unwrapping and filtering of the patterned wafer surface generates a lot of large phase unwrapping errors which limit the wafer geometry application.

It is contemplated that the small patch phase unwrapping and filtering process as described above is also very useful for obtaining local surface slopes for in-plane distortion (IPD) overlay error analysis of bare and patterned wafers. For instance, once the local surface slopes in x- and y-directions are calculated, they can be used to calculate overlay error and provide information for the overlay and leveling error analysis. It is contemplated that the small patch phase unwrapping and filtering process as described above can be used for various other purposes, such as wafer surface nanotopography analysis, overlay error analysis with local slope maps, stress analysis with the local curvature maps and the like without departing from the spirit and scope of the present disclosure. It is also contemplated that the local phase unwrapping methods described above can be used directly in the selected wafer regions to perform the high quality defect detection and quantification, without using the amplitude map.

It is contemplated that the defect detection processes as described above can be implemented in various wafer metrology tools and interferometer systems, such as Wafer-Sight metrology system from KLA-Tencor. Some of the advantages of the systems and methods described above are reiterated here again for illustrative purposes. It is noted that amplitude maps can be generated and used to perform defect detection and avoid errors associated with conventional global phase unwrapping. However, amplitude maps themselves cannot provide very useful height and depth information of the detected defects. By using the amplitude and local phase unwrapping, the problems associated with global phase unwrapping can be avoided and the height and depth information of the detected defects can be provided as well. The combined use of amplitude map and local unwrapped map can also allow the better feature/defect detection by using both the feature amplitude and phase maps, since very helpful complementary defect contrast information can be obtained.

In addition, the local phase unwrapping and filtering described above for both one-dimensional and two-dimensional processes can be used directly for high quality detection and quantification of the surface defects, without using the amplitude map. In many applications, such as slipline detection, this method can provide even better results than from the amplitude map because the phase contrast may be greater than the amplitude contrast for such defects. Furthermore, the local phase unwrapping and filtering processes as described above can be used to generate the whole wafer map, reducing errors compared to conventional global phase unwrapping and providing local slope information for pattern overlay analysis, local curvature for surface stress analysis, or general surface shape variation for nanotopography analysis, as well as other applications.

It is contemplated that while the examples above referred to wafer inspections, the systems and methods in accordance with the present disclosure are applicable to other types of polished plates as well without departing from the spirit and scope of the present disclosure. The term wafer used in the present disclosure may include a thin slice of semiconductor material used in the fabrication of integrated circuits and other devices, as well as other thin polished plates such as magnetic disc substrates, gauge blocks and the like.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A method for inspecting a wafer, comprising:
measuring a set of intensity frames of at least one portion of a surface of the wafer utilizing at least one phase-shifting interferogram detector of a wafer inspection system;
extracting an amplitude map of said at least one portion of the surface of the wafer based on said set of intensity frames with a wafer surface feature detection module executed by an interferometer system;
performing wafer defect detection based on the amplitude map with the wafer surface feature detection module executed by the interferometer system;
quantifying at least one of: a shape, a height, a depth, an area and a volume of a detected defect of the wafer; and
reporting data regarding the detected defect of the wafer and said at least one of: the shape, the height, the depth, the area and the volume of the detected defect of the wafer.

2. The method of claim 1, wherein the at least one phase-shifting interferogram detector includes two phase-shifting interferometer devices positioned on diametrically opposite sides of a cavity defined to receive the wafer, wherein the two phase-shifting interferometer devices are configured to simultaneously acquire intensity frames of at least one portion of both a front surface and a back surface of the wafer.

3. The method of claim 1, further comprising:
extracting a phase map of said at least one portion of the surface of the wafer based on said set of intensity frames; and
performing defect detection based on at least one of: the amplitude map and the phase map.

4. The method of claim 3, wherein extracting a phase map of said at least one portion of the surface of the wafer based on said set of intensity frames further comprises:
unwrapping the phase map local to a detected defect area utilizing at least one of: a local one-dimensional phase unwrapping process and a local two-dimensional phase unwrapping process.

5. The method of claim 1, wherein the data regarding the detected defect of the wafer and said at least one of: the shape, the height, the depth, the area, and the volume of the detected defect of the wafer is reported to facilitate control of manufacturing of the wafer.

6. A method for inspecting a wafer, comprising:
measuring a set of intensity frames of a surface of the wafer utilizing at least one phase-shifting interferogram detector of a wafer inspection system;
extracting a phase map of at least one region of interest of the surface of the wafer based on said set of intensity frames with a wafer surface feature detection module executed by an interferometer system;
unwrapping the phase map utilizing a local one-dimensional phase unwrapping process, wherein the local one-dimensional phase unwrapping process is performed based on a plurality of linear unwrapping paths defined locally within said at least one region of interest with a phase unwrapping module executed by the interferometer system;
performing wafer defect detection based on the unwrapped phase map with the wafer surface feature detection module executed by the interferometer system;
quantifying at least one of: a shape, a height, a depth, an area, and a volume of a detected defect of the wafer; and reporting data regarding the detected defect of the wafer and said at least one of: the shape, the height, the depth, the area, and the volume of the detected defect.

7. The method of claim 6, wherein the at least one phase-shifting interferogram detector includes two phase-shifting interferometer devices positioned on diametrically opposite sides of a cavity defined to receive the wafer, wherein the two phase-shifting interferometer devices are configured to simultaneously acquire intensity frames of at least one portion of both a front surface and a back surface of the wafer.

8. The method of claim 6, further comprising:
filtering the unwrapped phase map prior to performing defect detection.

9. The method of claim 6, further comprising:
extracting an amplitude map based on said set of intensity frames; and
identifying said at least one region of interest at least partially based on the amplitude map.

10. The method of claim 6, wherein the data regarding the detected defect of the wafer and said at least one of: the shape, the height, the depth, the area, and the volume of the detected defect of the wafer is reported to facilitate control of manufacturing of the wafer.

11. A method for inspecting a wafer, comprising:
measuring a set of intensity frames of a surface of the wafer utilizing at least one phase-shifting interferogram detector of a wafer inspection system;
extracting a phase map of at least one region of interest of the surface of the wafer based on said set of intensity frames with a wafer surface feature detection module executed by an interferometer system;
unwrapping the phase map utilizing a local two-dimensional phase unwrapping process, wherein the local two-dimensional phase unwrapping process is performed locally for said at least one region of interest with a phase unwrapping module executed by the interferometer system;
performing wafer defect detection based on the unwrapped phase map with the wafer surface feature detection module executed by the interferometer system;
quantifying at least one of: a shape, a height, a depth, an area, and a volume of a detected defect of the wafer; and
reporting data regarding the detected defect of the wafer and said at least one of: the shape, the height, the depth, the area, and the volume of the detected defect of the wafer.

12. The method of claim 11, wherein the at least one phase-shifting interferogram detector includes two phase-shifting interferometer devices positioned on diametrically opposite sides of a cavity defined to receive the wafer, wherein the two phase-shifting interferometer devices are configured to simultaneously acquire intensity frames of at least one portion of both a front surface and a back surface of the wafer.

13. The method of claim 11, further comprising:
filtering the unwrapped phase map prior to performing defect detection.

14. The method of claim 11, further comprising:
extracting an amplitude map based on said set of intensity frames; and
identifying said at least one region of interest at least partially based on the amplitude map.

15. The method of claim 11, wherein the data regarding the detected defect of the wafer and said at least one of: the shape, the height, the depth, the area and the volume of the detected defect of the wafer is reported to facilitate control of manufacturing of the wafer.

16. The method of claim 11, wherein said at least one region of interest includes a plurality of regions of interest jointly covering the full surface of the wafer, further comprising:
unwrapping the phase map utilizing a local two-dimensional phase unwrapping process for each of the plurality of regions of interest;
filtering the unwrapped phase maps for the plurality of regions of interest; and
integrating the unwrapped and filtered phase maps for the plurality of regions of interest to form a continuous unwrapped and filtered phase map for the full surface of the wafer.

17. A wafer inspection system, comprising:
at least one phase-shifting interferogram detector configured for acquiring a set of intensity frames of a surface of a wafer in a wafer inspection process; and
at least one processor in communication with the interferometer, the at least one processor configured to execute a set of instructions that enables the at least one processor to:
extract an amplitude map of the surface of the wafer based on said set of intensity frames;
perform wafer defect detection based on the amplitude map;
quantify at least one of: a shape, a height, a depth, an area, and a volume of a detected defect of the wafer; and
report data regarding the detected defect of the wafer and said at least one of: the shape, the height, the depth, the area, and the volume of the detected defect of the wafer.

18. The system of claim 17, wherein the at least one processor is further configured to:
identify at least one region of interest based on the amplitude map;
extract a phase map of the at least one region of interest;
unwrap the phase map utilizing a local phase unwrapping process; and
perform said defect detection at least partially based on the phase map.

19. The system of claim 18, wherein the phase map is unwrapped utilizing a local one-dimensional phase unwrapping process, wherein the local one-dimensional phase unwrapping process is performed based on a plurality of linear unwrapping paths defined within said at least one region of interest.

20. The system of claim 18, wherein the phase map is unwrapped utilizing a local two-dimensional phase unwrapping process, wherein the local two-dimensional phase unwrapping process is performed for said at least one region of interest.

21. The system of claim 17, wherein said at least one region of interest includes a plurality of regions of interest jointly covering the full surface of the wafer, and wherein the phase map is unwrapped utilizing a local two-dimensional phase unwrapping process for each of the plurality of regions of interest.

22. The system of claim 21, wherein the unwrapped phase maps for the plurality of regions of interest are filtered and integrated to form a continuous unwrapped and filtered phase map for the full surface of the wafer.

23. The system of claim 17, wherein the at least one processor is further configured to:
filter the unwrapped phase map prior to defect detection.

24. The system of claim 17, wherein the data regarding the detected defect of the wafer and said at least one of: the shape, the height, the depth, the area, and the volume of the detected defect of the wafer is reported to facilitate control of manufacturing of the wafer.

25. The system of claim 17, wherein the at least one phase-shifting interferogram detector includes two phase-shifting interferometer devices positioned on diametrically opposite sides of a cavity defined to receive the wafer, wherein the two phase-shifting interferometer devices are configured to simultaneously acquire intensity frames of at least one portion of both a front surface and a back surface of the wafer.

* * * * *